United States Patent [19]
Kanzaka et al.

[11] Patent Number: 5,680,473
[45] Date of Patent: Oct. 21, 1997

[54] SURFACE INSPECTION DEVICE

[75] Inventors: Takashi Kanzaka; Yuji Kozuka, both of Kanagawa-ken; Osamu Sugihashi, Tokyo, all of Japan

[73] Assignees: Nippon Mining & Metals Co., Ltd.; Hajime Industries Ltd., both of Tokyo, Japan

[21] Appl. No.: 563,132

[22] Filed: Nov. 27, 1995

Related U.S. Application Data

[63] Continuation of Ser. No. 295,474, Aug. 24, 1994, abandoned, which is a continuation of Ser. No. 94,532, Jul. 20, 1993, abandoned, which is a continuation of Ser. No. 902,416, Jun. 19, 1992, abandoned, which is a continuation of Ser. No. 628,382, Dec. 14, 1990, abandoned.

[30] Foreign Application Priority Data

Dec. 19, 1989 [JP] Japan .................. 1-328917

[51] Int. Cl.$^6$ ........................................ G06K 9/00
[52] U.S. Cl. ........................................ 382/141
[58] Field of Search .................. 382/106, 110, 382/141, 142, 143, 146, 147, 209, 218, 282; 358/101, 106, 107; 356/429, 430

[56] References Cited

U.S. PATENT DOCUMENTS

| | | | |
|---|---|---|---|
| 3,955,179 | 5/1976 | Planke | 382/142 |
| 4,055,834 | 10/1977 | Planke | 382/142 |
| 4,296,405 | 10/1981 | Rich | 382/110 |
| 4,414,566 | 11/1983 | Peyton et al. | 382/142 |
| 4,500,202 | 2/1985 | Smyth | 382/147 |
| 4,587,617 | 5/1986 | Barker et al. | 382/34 |
| 4,679,075 | 7/1987 | Williams et al. | 358/106 |
| 4,692,943 | 9/1987 | Pietzsch et al. | 382/55 |
| 4,735,323 | 4/1988 | Okada et al. | 382/110 |
| 4,969,038 | 11/1990 | Lemelson | 382/141 |
| 4,969,199 | 11/1990 | Nara | 382/146 |
| 4,972,494 | 11/1990 | White et al. | 382/143 |
| 5,007,096 | 4/1991 | Yoshida | 382/142 |
| 5,027,295 | 6/1991 | Yotsuya | 382/8 |
| 5,046,111 | 9/1991 | Cox et al. | 382/143 |
| 5,128,753 | 7/1992 | Lemelson | 382/141 |

Primary Examiner—Jose L. Couso
Attorney, Agent, or Firm—Bauer & Schaffer

[57] ABSTRACT

Apparatus for inspecting the surface of objects such as band-like running material, which may be metal, paper, or textile, without stopping or reducing the speed of the inspection line, to determine the occurrence of defects. The inspected object surface image and defect data are recorded so that at a desirable later time, the defect data may be reviewed to make a judgement of acceptance or rejection of the object. The apparatus provides an effective control on production.

1 Claim, 2 Drawing Sheets

SURFACE INSPECTION DEVICE

This is a Continuation of Ser. No. 08/295,474, filed Aug. 24, 1994 now abandoned, which is a continuation of Ser. No. 08/094,532, filed Jul. 20, 1993 now abandoned, which is a continuation of Ser. No. 07/902,416 filed Jun. 19, 1992 now abandoned, which is a continuation of Ser. No. 07/628,382 filed Dec. 14, 1990 now abandoned.

BACKGROUND OF THE INVENTION

1. Field of the Invention

The present invention relates generally to surface inspection apparatuses that photosence an object to be inspected by a pick-up camera such as a video camera and process its output video signal by electronic processors such as inspection machines, to thereby conduct a surface inspection of the object in order to inspect the flaws or dirty on its surface or judge the extistence or not of defects, and especially to a surface inspection apparatus in which when defects exist on the surface of the object such as band-shaped metal, paper or textile or the like, such a video signal including the defect information is automatically recorded, so that the video signal containing the defect may be reproduced on the picture screen of a monitor when necessary in order that visual judgement of the defect classification as good or bad can be made while the video signal is utilized as production control data.

2. Description of the Prior Art

Conventionally, upon conducting surface inspection for substance such as metal, paper or textile in long band conditions, in order to confirm the classification of the surface defect to be good or bad defect by the human eye, the inspection line of the substance had to be intermittently stopped, or line speed reduced in order to confirm such defect in order to make the acceptance judgements. Therefore, in the practical surface inspection of the prior art, there were the following limitations.

(1) The inspection line speed cannot be raised.

(2) Due to the line stoppage or speed reductions in order to conduct inspection, the substance to be inspected is apt to be damaged.

(3) Due to the line stoppage or speed reductions in order to conduct inspection, it is impossible to incorporate the same into the continuous processing lines.

(4) The operators cannot be involved with jobs or assignments other than surface inspection when the inspection is under operation.

OBJECTS AND SUMMARY OF THE INVENTION

Therefore, it is an objects of the present invention to propose a surface inspection apparatus for substance that will automatically detect the surface defects on the substance, and when defect detection is made, the video signal of the inspected subject containing the defect data be automatically recorded so that such video signal containing the defect can be reproduced on a picture screen of a monitor when necessary, so that visual confirmation of the defect judgement as good or bad can be made.

According to an aspect of the present invention, there is provided an apparatus for inspecting the surface of an object, in which a video camera photosense the object and a video signal therefrom is processed by an inspection machine that has a defect detector so that the existence or not of defects on the surface of the inspected object is inspected, which comprises:

a position data generator provided in relation with a feeder of the object for generating a supply length data of the inspected object;

a video processor, to which the position data and detection signals from the position data generator and the defect data are supplied, for generating data of defects; and a printer, to which the data is supplied, for producing a deployment chart as a printout on which the defect data is printed.

According to another aspect of the present invention, there is provided an apparatus for inspecting the surface of an object, in which a video camera photosense the object and a video signal therefrom is processed by an inspection machine that has a defect detector so that the existence or not of defects on the surface of the inspected object is inspected, which comprises:

a position data generator provided in relation with a feeder of the object for generating a supply length data of the inspected object;

a video processor, to which the position data and detection signals from the position data generator and the defect data are supplied, for generating data of defects;

a data composer, to which video signals from the video camera as well as data from the video processor are supplied, for providing a composed signal of the video signal and the data;

a video signal recorder, to which the composed signal is supplied, for recording the composed signal on a recording medium;

a video signal reproducer for reproducing the recorded composed signal from the recorder; and a displayer for displaying thereon a reproduced signal by the reproducer.

The additional, and other objects, features and advantage of the present invention will become apparent from the following description taken in conjunction with the accompanying drawings.

DESCRIPTION OF THE PREFERRED EMBODIMENT

An example of the present invention will be explained hereunder in reference to the attached drawings.

Figure 1:
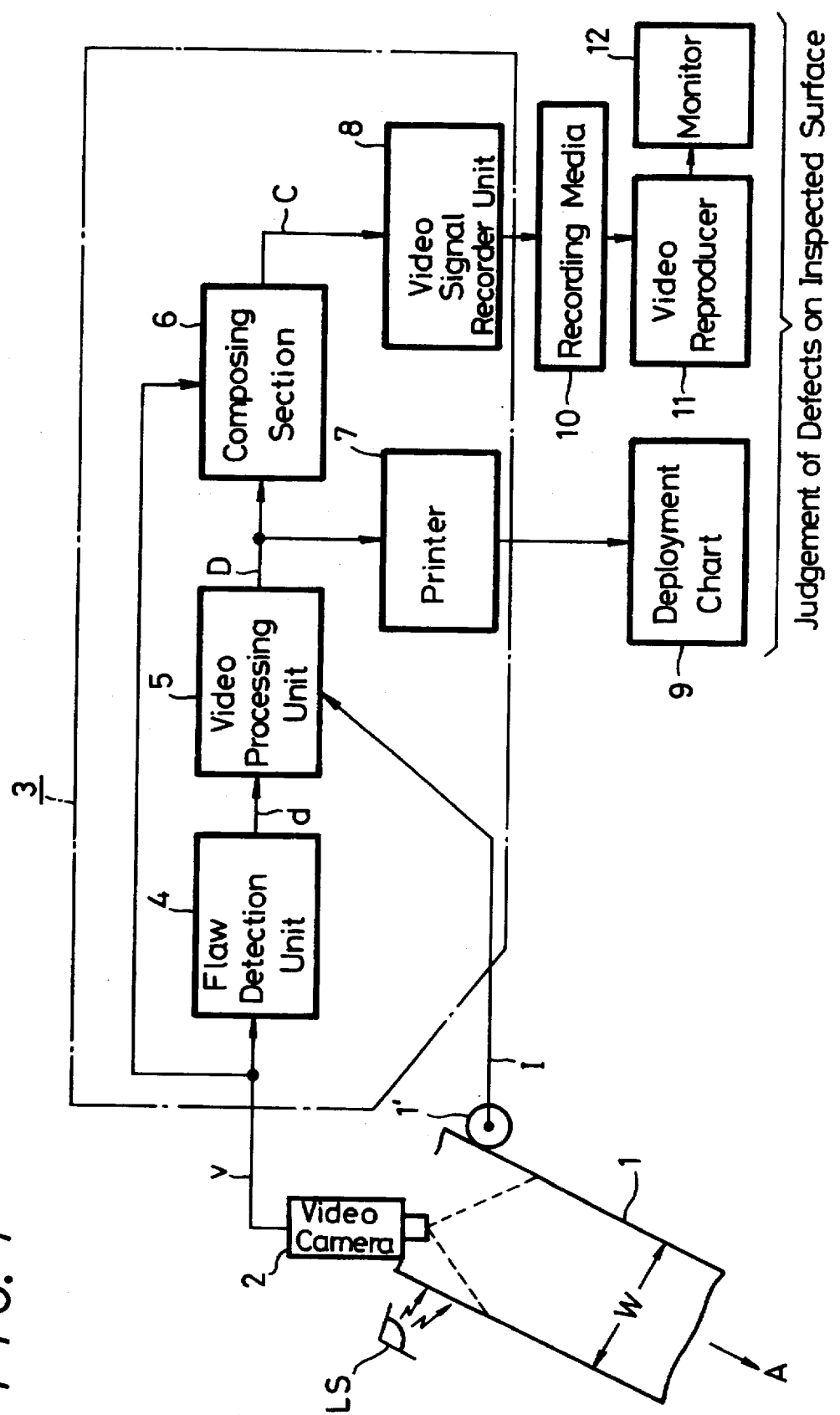
FIG. 1 is a systematic block diagram that shows an example of the present invention.

FIG. 1 is a block diagram that shows an embodiment of the surface inspection apparatus according to the present invention. In FIG. 1, although it is not entirely shown on the drawing, reference numeral 1 designates an object to be inspected such as a long band-shaped metal or paper, textile or the like. This inspected object 1 is irradiated by a light source LS and then the surface of the object 1 is photosensed by a video camera 2 such as a television camera or the like. An image or video signal v from the video camera 2 is processed by an inspection machine 3 that is an electronic processor to inspect the existence or not of defects such as flaws, dirty or the like on the surface the inspected object 1.

As the next step, the inspection machine 3 shall be explained.

The output video signal v from the video camera 2 is supplied to a flaw defection unit 4. This flaw detection unit 4 outputs a flaw detection signal d, only when there is a defect such a flaws, dirty or the like on the surface of the inspected object 1. This detection signal d is supplied to a video processing unit 5. This video processing unit 5 processes the detection signal d and produces necessary data D related to surface defects on the inspected object 1, such as the location thereof in the width direction of the inspected object 1 as well as size thereof, etc.

This data D is supplied to a printer 7. Then, this printer 7 prints out a deployment chart 9 which indicates the defect location or the like on a print paper 9' as shown on FIG. 2. Further, on FIG. 2, reference letter W' denotes the width of the deployment chart 9 on the print paper 9' that responds to the width W of the inspected object 1 as shown on the FIG. 1, whereas reference letter A' is the feeding direction of the deployment chart 9 which corresponds to the transfer direction A of the inspected object 1 on FIG. 1. Further, in FIG. 2, X marks and O marks indicate the defects such as flaws or the like on the inspected object 1. In this case, the X marks designate such defects that cannot be overlooked while the O marks denote the defects that may be ignored. For this reason, at each of the marks, the symbols that indicate the sizes of defects such as A1, A2, A3, A4, are printed. Also, as shown on FIG. 2, on the deployment chart 9, along its width direction W' there are scale marks such as in mm. units, so that the location of such X marks and O marks of the defects in the width direction W' are obviously indicated.

Figure 2:
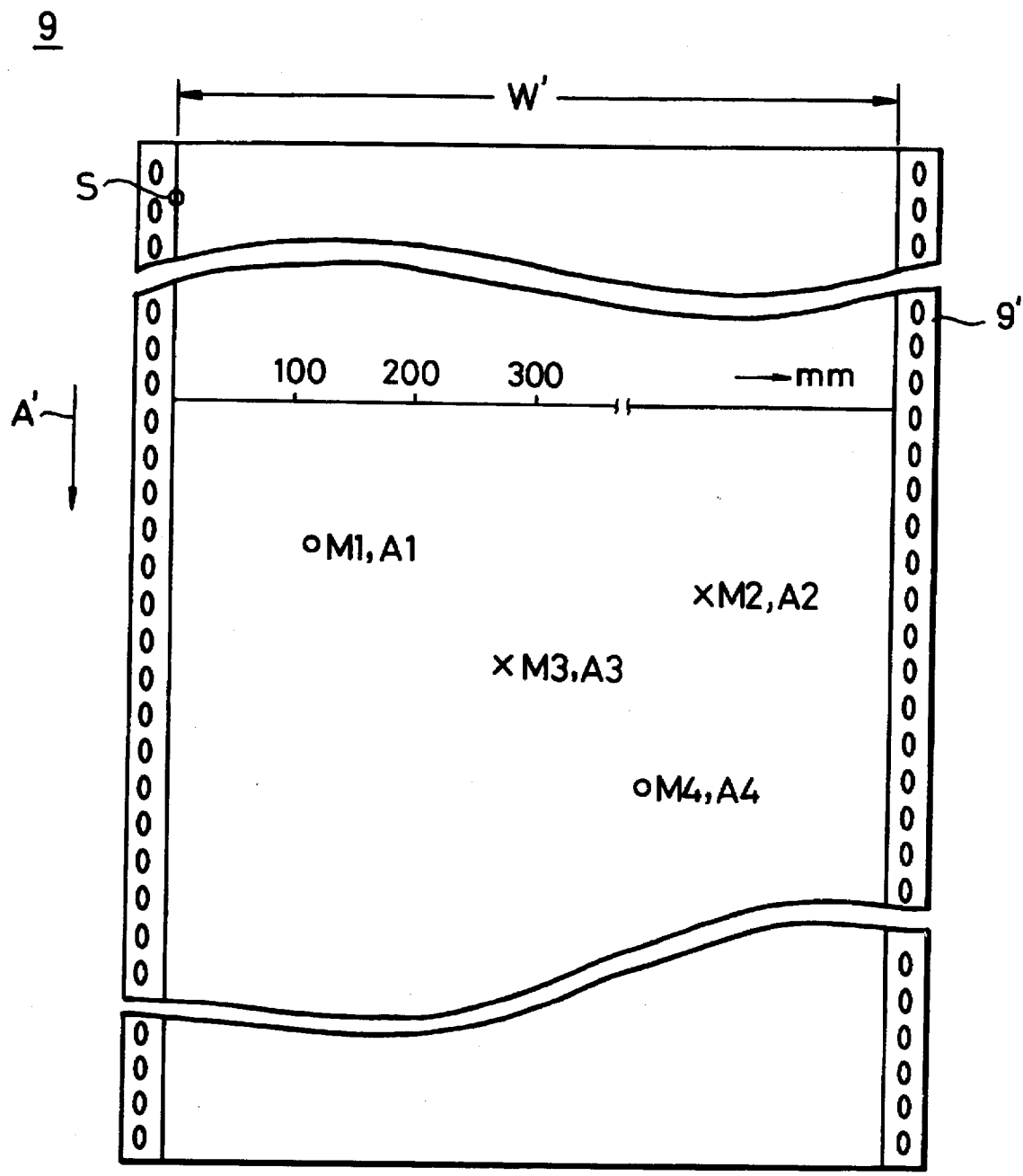
FIG. 2 is a top view of such deployment chart.

Further, in FIG. 2, reference better S indicate the inspection start position of the inspected object 1. Needless to say, in this case as necessary, it is accepted to print the other data not limited to the defect position in the width direction W' on the deployment chart 9 as stated above.

Going back to FIG. 1, the data D from the video processor unit 5 as based on the defect detection signal d, is also supplied to a composing unit 6. To this composing unit 6, the video signal v from the video camera 2 is also supplied. Accordingly, at the composing section 6, the video signal v and the data D from the video processor unit 5 are mixed to provide a composing signal C which is delivered to a video signal recorder unit 8. This video signal recorder unit 8 utilizes a recording media 10 such as a video floppy disc or the like, to record the composing signal C formed of the data D and video signal v. In that event, this recording media 10 need not be specified as long as the recorded data can be reproduced as a static image. Also, in the data D composed with the video signal v, if such other important data not only limited to the defect position on the inspected object 1, but also such data as the inspection date, product type, lot number etc as an example, are also contained, it will be informative at the time of recorded video signal reproduction.

Further, as mentioned above,the video processor unit 5 produces data D which contains the flaw or defect position in the width direction W and inputs the same to the composing unit 6 and printer 7, but in the position data to be sent to the deployment chart 9 shown in FIG. 2 or the video signal recorder 8, the data in the length direction of the inspected object 1 is also contained. For such purpose, to the drive shaft (not shown on drawings) of the conveyer roll for the object 1, as shown on FIG. 1, a position detector 1' such as a rotary encoder or the like is coupled, which will send a position data I as related to the run distance of the inspected object 1 from the inspection start position S to the video processor unit 5 constantly, so that when a defect is detected, the distance (in meter units as an example) from the inspection start position S to that time is calculated by the video processor unit 5 and such distance data will be contained in the data D.

This data M in the lengthwise direction (Feed Direction A) of the inspected object 1 is printed, as shown on FIG. 2, adjacent the respective X marks and O marks in, for example, the direction of width W' that respond to the defects, as marks M1, M2, M3, and M4, whereas the large or small defect size data A1, A2, A3 and A4 are also printed at sides of M1–M4 data, respectively. Therefore, by looking at the deployment chart 9, the existence or not of defects on the surface of the inspected object 1, with such sizes and the defect position on the inspected object 1 in the direction of its width W' and length direction are readily apparent.

Further, the printer 7 does not constantly run recording material 9' such as recording paper for the deployment chart 9, but when there is a defect at the defect detector unit 4, in response to the data D from the video processor unit 5, feeds a predetermined amount of the recording material 9' only and as shown on FIG. 2, the defect data shall be printed thereon.

Accordingly, there is no waste of the recording material 9' (paper for printing) for the deployment chart 9, so that effective use thereof is made. Also, similarly to the video signal recorder 8, only the signal C at the time when defects are detected is intermittently recorded so that such recording media 10 such as a floppy disc may have the minimum usage.

The recording media 10 such as a floppy disc will normally be able to record the images of about 50 sheets of the inspected object 1 so that during or after the inspection, as shown on FIG. 1, such recorded video signal is reproduced by a video reproducer 11 from the recording media 10 and then is displayed on a monitor 12. Then if the displayed image is compared with the deployment chart 9 as printout by the printer 7, an accurate judgement to the acceptance or rejection of the defect on the inspected object 1 can be made. For instance, depending upon the position, size and so on of the defects, it is possible to sort the grades of the defects on the inspected object 1.

The above-mentioned description is given on one example of the present invention and it will be apparent that many modification and variations could be effected by one skilled in the art without departing from the spirits or the scope of the novel concepts of the present invention so that the spirit or scope of the invention should be determined by the appended claims only.

We claim as our invention:

1. Apparatus for inspecting the surface of an object in the shape of an elongated band, comprising means for continuously conveying the band from its front end to its rear end in a linear direction through an inspection station, said inspection station having an initial feed position, a video camera for constantly viewing the surface of said band at said initial feed position, and an inspection device, said inspection device comprising a defect detector for sensing the existence of defects on the viewed surface of said band and providing a signal thereof; a position data generator for generating a position data signal indicative of the distance said band moves from the initial feed position; processor means receiving the position data signal and the signal from said defect detector for producing a defect data signal when a defect exists; composer means receiving the video signal from said video camera and the produced defect data signal from said video processor for producing a composed signal combining said video signal and said produced defect data signal, said composed signal being indicative of the shape and size of said band, the shape and size of said defects and the position of said existing defects on the surface of said band; a signal recorder for recording said composed signal on a recording medium only when said defects are detected; a video signal reproducer for reproducing the recorded composed signal from said recorder; and means for displaying the data reproduced by said video signal reproducer, including means for detecting from said video output signal the existence of a defect on the surface of said object and providing a signal thereof, means for receiving the position data signal and the defect signal and providing a defect-position data signal indicative of both the defect signal and the position data signal, a deployment chart corresponding to the surface of said object in its shade and size and having scale marks in a width direction of said deployment chart and an inspection start mark, means for feeding said deployment chart by a predetermined amount when the defect signal is received and for recording on said chart the defect-data indicative of the shape and size of the defect at the corresponding positions at which said defects are detected.

* * * * *